United States Patent [19]

Kitson et al.

[11] Patent Number: 4,826,795
[45] Date of Patent: May 2, 1989

[54] CATALYST FOR THE PRODUCTION OF AN ALCOHOL AND/OR A CARBOXYLIC ACID ESTER BY HYDROGENATION OF A CARBOXYLIC ACID

[75] Inventors: Melanie Kitson, Staines; Peter S. Williams, Hull, both of England

[73] Assignee: BP Chemicals Limited, London, England

[21] Appl. No.: 197,579

[22] Filed: May 5, 1988

Related U.S. Application Data

[62] Division of Ser. No. 848,998, Apr. 7, 1986, Pat. No. 4,777,303.

[30] Foreign Application Priority Data

Apr. 13, 1985 [GB] United Kingdom ............... 8509530

[51] Int. Cl.$^4$ .................. B01J 21/18; B01J 23/28; B01J 23/30; B01J 23/40
[52] U.S. Cl. .............................. 502/184; 502/183; 502/185
[58] Field of Search ................ 502/313, 183, 185, 184

[56] References Cited

U.S. PATENT DOCUMENTS

| | | | |
|---|---|---|---|
| 2,322,095 | 6/1943 | Schmidt | 568/885 |
| 2,861,959 | 11/1958 | Thorn et al. | 502/313 |
| 3,363,009 | 1/1968 | Schuman et al. | 568/885 |
| 3,536,632 | 10/1970 | Kroll | 568/885 |
| 3,661,769 | 5/1972 | Venuto et al. | 502/313 X |
| 3,770,658 | 11/1973 | Ozaki et al. | 502/243 |
| 3,829,448 | 8/1974 | Kanetaka et al. | 568/885 |
| 4,359,404 | 11/1982 | Grey et al. | 568/885 |
| 4,456,775 | 6/1984 | Trainer et al. | 568/885 |
| 4,500,650 | 2/1985 | Wyatt et al. | 502/313 X |

FOREIGN PATENT DOCUMENTS

| | | | |
|---|---|---|---|
| 433549 | 8/1935 | United Kingdom . | |
| 457358 | 11/1936 | United Kingdom | 568/885 |

OTHER PUBLICATIONS

Sokolskii et al., "Catalyst for the Hydrogenation of Organic Compounds", USSR 420,326 (Chemical Abstracts, vol. 81, p. 354, 1974, Abstract No. 96797m).
Above References L and R were cited by applicants.

*Primary Examiner*—E. J. Shine
*Attorney, Agent, or Firm*—Brooks, Haidt Haffner & Delahunty

[57] ABSTRACT

An alcohol and/or a carboxylic acid ester is (are) produced from a $C_2$ to $C_{12}$ carboxylic acid by contacting the carboxylic acid at elevated temperature and pressure with hydrogen in the presence of a heterogeneous catalyst characterized in that the catalyst comprises a first component which is either molybdenum or tungsten and a second component which is a noble metal of Group VIII of the Periodic Table of the Elements, optionally on a support, for example a high surface area graphitized carbon.

10 Claims, No Drawings

CATALYST FOR THE PRODUCTION OF AN ALCOHOL AND/OR A CARBOXYLIC ACID ESTER BY HYDROGENATION OF A CARBOXYLIC ACID

This is a division of application Ser. No. 848,998, filed Apr. 7, 1986, now U.S. Pat. No. 4,777,303.

The present invention relates to the catalysed hydrogenation of carboxylic acid ester.

The hydrogenation of carboxylic acids to produce the corresponding alcohol in the presence of heterogeneous catalysts is known from, for example, U.S. Pat. No. 4,524,225, U.S. Pat. No. 4,104,478, GB-A-1534232, GB-A-1551741, DE-A-3221077 and EP-A-147219.

U.S. Pat. No. 4,524,225 describes the hydrogenation of $C_6$–$C_{24}$ fatty acids by contacting the fatty acid with hydrogen at 100° to 300° C. and 100 to 3000 psig in the presence of a zerovalent metal selected from Cu, Cr, Ru, Pt, Pd, Re and mixtures thereof dispersed on a support which may be alpha, theta or titanated alumina, titania, or $AlPO_4$ or a mixture thereof.

U.S. Pat. No. 4,104,478 describes the production of $C_4$ to $C_{24}$ fatty alcohols by catalytically hydrogenating the corresponding fatty acid at 170° to 250° C. and 20 to 140 atmospheres over a catalyst system consisting of (a) 1 part wt. of activated Re, and (b) 0.25 to 1.5 parts of an extrinsic metal catalyst selected from Ru, Rh, Pt and Pd.

GB-A-1534232 describes the preparation of alcohols by catalytic hydrogenation of carboxylic acids at elevated temperature and pressure in the presence of water and/or solvents using a Pd/Re catalyst on a support, the catalyst having a Pd:Re wt ratio of 0.01 to 5:1.

GB-A-1551741 describes the one-step preparation of 1,4-butanediol from maleic acid by hydrogenation in the presence of a catalyst containing (A) elements of Group VII, preferably Mn or Re, or their compounds, and (B) elements of Group VIII, preferably Ru, Rh, Pd, Os, Ir or Pt, more preferably Pd or Pt or their compounds or mixtures thereof.

DE-A-3221077 describes the continuous production of ethanol by the hydrogenation of acetic acid at elevated pressure and temperature using a catalyst based on Co.

EP-A-147219, published after the priority date claimed for the subject application on an application claiming an earlier priority date, describes the hydrogenation of maleic acid using a Pd/Re/C catalyst.

We have now found novel catalysts for the hydrogenation of $C_2$ to $C_{12}$ carboxylic acids.

Accordingly the present invention provides a process for the production of an alcohol and/or a carboxylic acid ester from a $C_2$ to $C_{12}$ carboxylic acid by contacting the carboxylic acid at elevated temperature and pressure with hydrogen in the presence of a heterogeneous catalyst characterised in that the catalyst comprises a first component which is either molybdenum or tungsten and a second component which is a noble metal of Group VIII of the Periodic Table of the Elements.

In addition to the alcohol, the process of the invention generally also produces the corresponding ester as a by-product, for example the hydrogenation of acetic acid generally also produces ethyl acetate and the hydrogenation of propionic acid generally also produces propyl propionate. The proportion of the ester in the product will depend on the nature of the catalyst, for example tungsten-containing catalysts will generally produce higher proportions of the ester, and on the reaction conditions, for example the formation of esters is favoured by operating at low conversions, for example less than 50% per pass. The proportion of ester in the product may be further increased, if desired, by feeding additional carboxylic acid and/or by introducing an acidic function into the catalyst to promote 'in situ' esterification. It is possible, therefore, to produce a product substantially comprising the carboxylic acid ester, particularly by operating in the liquid phase at low conversions, for example less than 50%.

As the $C_2$ to $C_{12}$ carboxylic acid there may suitably be used either a saturated or an unsaturated carboxylic acid, preferably a saturated carboxylic acid. Both mono- and poly-basic carboxylic acids, for example dibasic carboxylic acids, may be employed. Suitable monobasic acids include acids having the formula R—COOH wherein R is a substituted or unsubstituted aliphatic, aromatic or araliphatic group, which acids are hydrogenated to alcohols of the formula $RCH_2OH$. Examples of suitable acids include acetic, propionic, butyric, heptanoic, succinic, glutaric, maleic and fumaric acids.

Hydrogen is commercially available on a large scale and may be used with or without further purification.

The catalyst comprises a first component which is either molybdenum or tungsten and a second component which is a noble metal of Group VIII. For the avoidance of doubt, the noble metals of Group VIII are the metals osmium, palladium, platinum, rhodium, ruthenium and iridium. Of the aforesaid metals palladium, rhodium and ruthenium are preferred. The catalyst preferably further includes, as a third component, a support. Suitable supports include high surface area graphitised carbons, graphites, silicas, aluminas and silica/aluminas, of which high surface area graphitised carbons and silicas are preferred.

Particularly suitable supports are the high surface area graphitised carbons described in GB-A-2136704. The carbon is preferably in particulate form e.g. as pellets. The size of the carbon particles will depend on the pressure drop acceptable in any given reactor (which gives a minimum pellet size) and reactant diffusion constraint within the pellet (which gives a maximum pellet size). The preferred minimum pellet size is 0.5 mm and the preferred maximum is 10 mm, e.g. not more than 5 mm.

The carbons are preferably porous carbons. With the preferred particle sizes the carbon will need to be porous to meet the preferred surface area characteristics.

Carbons may be characterised by their BET, basal plane, and edge surface areas. The BET surface area is the surface area determined by nitrogen adsorption using the method of Brunauer Emmett and Teller J. Am. Chem. Soc. 60,309 (1938). The basal plane surface area is the surface area determined from the heat of adsorption on the carbon of n-dotriacontane from n-heptane by the method described in Proc. Roy. Soc. A314 pages 473–498, with particular reference to page 489. The edge surface area is the surface area determined from the heat of adsorption on the carbon of n-butanol from n-heptane as disclosed in the Proc. Roy. Soc. article mentioned above with particular reference to page 495.

The preferred carbons for use in the present invention have a BET surface area of at least 100 $m^2/g$, more preferably at least 200 $m^2/g$, most preferably at least 300 m$^2$/g. The BET surface area is preferably not greater than 1000 m$^2$/g, more preferably not greater than 750 m$^2$/g.

The ratio of BET to basal plane surface area is preferably not greater than 4:1, more preferably not greater than 2.5:1. It is particularly preferred to use carbons with ratios of BET to basal plane surface area of not greater than 1.5:1.

It is preferred to use carbons with ratios of basal plane surface area to edge surface area of at least 10:1, preferably at least 100:1. It is not believed that there is an upper limit on the ratio, although in practice it will not usually exceed 200:1.

The preferred carbon support may be prepared by heat treating a carbon-containing starting material. The starting material may be an oleophilic graphite e.g. prepared as disclosed in GB 1,168,785 or may be a carbon black.

However, oleophilic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes not less than those indicated above as being preferred for the carbon support.

The preferred starting materials have the following characteristics: BET surface area of at least 100, more preferably at least 500 m$^2$/g.

The preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidising agent.

The duration of the heating in inert gas is not critical. The time needed to heat the carbon to the required maximum temperature is sufficient to produce the required changes in the carbon.

The oxidations step must clearly not be carried out under conditions such that the carbon combusts completely. It is preferably carried out using a gaseous oxidizing agent fed at a controlled rate to avoid over oxidation. Examples of gaseous oxidising agents are steam, carbon dioxide, and gases containing molecular oxygen e.g. air. The oxidation is preferably carried out to give a carbon weight loss of at least 10% wt based on weight of carbon subjected to the oxidation step, more preferably at least 15% wt.

The weight loss is preferably not greater than 40% wt of the carbon subjected to the oxidation step, more preferably not greater than 25% wt of the carbon.

The rate of supply of oxidizing agent is preferably such that the desired weight loss takes place over at least 2 hours, more preferably at least 4 hours.

Where an inert atmosphere is required it may be supplied by nitrogen or an inert gas.

Preferred silica supports are those having a high surface area, typically greater than 50m$^2$/g.

Suitably the catalyst comprises from 0.1 to 20% by weight, preferably from 1 to 10% by weight of the first component, from 0.1 to 20% by weight, preferably from 1 to 10% by weight of the second component, the remainder of the catalyst comprising a support.

The catalyst may be further modified by incorporation of a metal or metals of Group IA, Group IIA or Group IVA, preferably a metal of Group IA of the Periodic Table of the Elements. A suitable metal is potassium. The amount of the modifying metal(s) may suitably be in the range from 1 to 20% by weight, based on the total weight of the catalyst. The addition of the aforesaid modifying metals to the catalyst can have the advantageous effect that carbon-carbon bond hydrogenolysis can be suppressed to a greater or lesser extent during the carboxylic acid hydrogenation, thereby improving the selectivity of the process to desirable products.

The catalyst may suitably be prepared by any of the methods conventionally employed for the production of catalysts, for example by impregnation, including both co-impregnation and sequential impregnation, precipitation, including both co-precipitation and sequential precipitation, and by vapour deposition of the metals on the support. Techniques for effecting the aforesaid methods are well-known in the art and require no further elaboration.

A suitable method of producing a catalyst for use in the process of the present invention comprises the steps of:

(A) impregnating a support with a solution of a soluble noble metal compound thermally decomposable/reducible to the noble metal and subsequently removing the solvent therefrom, (B) heating the Group VIII noble metal on the support, and (C) impregnating the noble metal impregnated support with a solution of a soluble molybdenum or tungsten compound thermally decomposable/reducible to molybdenum or tungsten metal and/or oxide and thereafter removing the solvent therefrom.

Production of the catalyst in the aforesaid manner can avoid the noble metal impregnated on the support in step (A) being leached to any appreciable extent in step (C) of the process.

In this embodiment of the invention the solvent used in steps (A) and (C) of the process may be any suitable solvent, for example water.

The Group VIII noble metal on the support may suitably be heated in the presence of either an inert gas, for example nitrogen, a reducing gas, for example hydrogen, or an oxygen-containing gas, for example oxygen or air. Heating in the presence of an inert gas may suitably be accomplished at an elevated temperature in the range from 150° to 350° C. Heating in the presence of a reducing gas may suitably be accomplished at an elevated temperature in the range from 100° to 350° C. Heating in the presence of an oxygen-containing gas may suitably be accomplished at an elevated temperature in the range from 100° to 300° C., provided that when a high surface area graphitised carbon is used as support the upper temperature limit is 200° C.

Preferably, a further step is interposed between step (A) and step (B) wherein the Group VIII noble metal impregnated support is dried, suitably by heating at a temperature in the range from 50° to 150° C. It will be appreciated by those skilled in the art that this step may be incorporated into step (B), if desired.

Suitable molybdenum or tungsten compounds which are decomposable/reducible to the metal and/or oxide include salts of the metals and salts wherein the metals are present in the anionic moiety, for example, ammonium molybdate or ammonium tungstate. Suitable noble metal compounds which are decomposable/reducible to the noble metal include, for example, noble metal salts such as the carboxylates, halides and nitrates and ammonium salts containing the noble metal in the anion moiety, for example ammonium tetrachloropalladate.

The metal of Group IA, Group IIA or Group IVA of the Periodic Table of the elements may be added to the catalyst composition at any point during its preparation. Thus, the supported noble metal/molybdenum or tungsten catalyst may be impregnated with a solution of a soluble compound of the metal. Alternatively, a soluble compound of the metal may be added to the co-impregnation solution or either of the sequential impregnation solutions.

A preferred catalyst comprises palladium and molybdenum or tungsten supported on a high surface area graphitised carbon of the type described in the aforesaid GB-A-2136704.

Before use in the process of the invention the catalyst is preferably activated by contact at elevated temperature with either hydrogen or a hydrogen/inert gas, for example nitrogen, mixture, suitably for a period of from 1 to 20 hours. The elevated temperature may suitably be in the range from 200° to 350° C. Alternatively, the catalyst may be activated by heating to the reaction temperature in the presence of reactants.

Whilst the precise nature of the catalyst on the support can not be determined with any degree of confidence, it is believed that the Group VIII noble metal component is in the form of the elemental metal and the molybdenum or tungsten component is in the form of the elemental metal and/or an oxide thereof.

The process of the invention may suitably be operated at an elevated temperature in the range from 100° to 300° C., preferably from 150° to 250° C. The pressure may suitably be less than 50 bar.

The process may be operated in the liquid phase or the vapour phase.

The process may be operated batchwise or continuously, preferably continuously. The catalyst may be employed in the form of a fixed bed, a moving bed or a fluidised bed. The Gas Hourly Space Velocity for continuous operation may suitably be in the range from 50 to 50,000$^{-1}$, preferably from 2,000 to 30,000$^{-1}$.

In another aspect the present invention provides a catalyst for use in the process as hereinbefore described which comprises a first component which is either molybdenum or tungsten and a second component which is a noble metal of Group VIII of the Periodic Table of the Elements.

The invention will now be further illustrated by reference to the following Examples.

CATALYST PREPARATION

Catalysts were prepared according to the procedures outlined below. In these procedures the term "HSAG carbon" denotes high surface area graphitised carbon, prepared and characterised as follows:

The carbon used as support was prepared from a commercially available activated carbon sold by Degussa under the designation BK IV. The activated carbon was heat treated as follows. The carbon was heated from room temperature in a stream of argon to 1700° C. over a period of about one hour. When the temperature reached 1700° C. the carbon was allowed to cool in the stream of argon to 25° C. The carbon was then heated in air in a muffle furnace at approximately 520° C. for a time known from experience to give a weight loss of 20 %wt. The carbon was then heated in argon to between 1800° C. and 1850° C. in argon. The carbon was allowed to cool to room temperature in an argon atmosphere. The resulting graphite-containing carbon was then ground to 16-30 mesh BSS.

The resulting carbon had the following properties:
BET surface area: 710 m$^2$/g
basal plane surface area: 389 m$^2$/g
edge surface area: 2.3 m$^2$/g
BET/basal surface area ratio: 1.83
basal plane/edge surface area ratio: 169

EXAMPLE 1

In the following procedures nominal loading is defined as weight of *metal* (not salt) added to the support expressed as a percentage of the weight of support. A. An aqueous solution containing palladium nitrate and/or ammonium tungstate was added to HSAG carbon. The solvent was removed on a rotary evaporator, and the catalyst was then dried overnight at 100° C. in a vacuum oven. The amounts were chosen to give nominal loadings as follows: A1-2.5% Pd, 5% W; A2-5% W, (Pd excluded); and A3-5% Pd, (W excluded). A2 and A3 are not examples of catalysts for use in the process of the invention and are included only for comparison purposes.

B. The procedure above was repeated using ammonium molybdate instead of ammonium tungstate. The amounts of each component were chosen to give nominal loadings as follows: B1-2.5% Pd, 5.1% Mo; B2-5.1% Mo (Pd excluded). B2 is not an example of a catalyst for use in the process of the invention and is included only for comparison purposes.

C. An aqueous solution of palladium nitrate was added to HSAG carbon. The solvent was removed on a rotary evaporator, and the resulting impregnated carbon catalyst dried at 100° C. overnight in a vacuum oven. The catalyst was then transferred to a glass tube, and was then heated in a stream of hydrogen from ca 30° to 280° C. over a period of six hours. After ten hours at the final temperature, the catalyst was cooled under hydrogen and purged for several hours with nitrogen. The amount of palladium nitrate was chosen to give a nominal loading of 2.5% wt.

D. The catalyst from procedure C was mixed with an aqueous solution of ammonium tungstate, the solvent again removed a rotary evaporator, and the catalyst dried in a vacuum oven at 100° C. overnight. The amount of ammonium tungstate was chosen to give a nominal loading of 10% wt.

E. The procedure of D was employed, except that ammonium molybdate was used instead of ammonium tungstate. The molybdenum loading was nominally 10%.

F. An aqueous solution containing rhodium trichloride and ammonium tungstate was added to HSAG carbon. The procedure A above was then followed, to give a catalyst containing, nominally, 5% Rh and 5% W.

CATALYST TESTING

For vapour phase experiments at pressures in the range 1-11 barg, 2.5 mls of catalyst was loaded into a corrosion resistant stainless steel tube of internal diameter 6-7 mm, and the tube assembly placed in a tubular furnace. The catalyst was then activated at either 280° or 300° C. over a two hour period, and then holding at the final temperature for one hour. After activation, the catalyst was cooled in hydrogen to the desired reaction temperature. A mixture of carboxylic acid vapour and hydrogen was then passed over the catalyst, and pressure was adjusted to the required value by means of a back-pressure regulator. The vapour/hydrogen mixture was formed in a vapourising zone, to which acetic acid liquid and hydrogen gas were separately metered. The product vapors and gases leaving the reactor were sampled on-line and analysed by gas-liquid chromatography (glc).

Temperature was measured by means of a thermocouple inserted into the catalyst bed.

The product mixtures typically contained the appropriate alcohol and ester (the latter formed by esterification of alcohol with unreacted acid), together with traces of the appropriate dialkyl ether, and aldehyde, and by product methane and ethane. In general, with carbon and silica supported catalysts, the main product is alcohol, especially at high conversions and/or in the vapour phase.

For the purposes of the examples, conversions and selectivities have been calculated as, respectively, the proportion of carboxylic acid hydrogenated, and the proportion of the hydrogenated carboxylic which is not converted into alkane by product. Thus, selectively denotes the ability of the catalyst to carry out hydrogenation without alkanation. In all examples (unless stated otherwise) only trace amounts ($\leq 2\%$) of dialkyl ether and aldehyde are formed.

DEFINITIONS

WHSV=Weight Hourly Space Velocity=kg liquid feed per kg catalyst per hour.

LHSV=Liquid Hourly Space Velocity=liters of liquid feed per liter of catalyst per hour.

Productivity=kg acid converted per kg catalyst per hour.

EXAMPLES 2-8

The catalysts of procedures A and B of Example 1 were tested for activity in the hydrogenation of acetic acid at 10.3 barg. The WHSV was ca 1.1 (LHSV=0.35), and the ratio acetic acid to hydrogen was ca 1:11 molar. Results are reported in Table 1.

TABLE 1

| Example | Catalyst | T/°C. | Conversion (%) | Selectivities (%) alcohol + ester | ether | Ratio (molar) alcohol:ester |
|---|---|---|---|---|---|---|
| 2 | A1 | 189 | 16.5 | 84.3 | 13.0 | 0.06 |
| 3 | A2 | 203 | 0.3 | — | — | — |
| 4 | A3 | 200 | 0.6 | — | — | — |
| 5 | B1 | 189 | 10.6 | 86.6 | 0.8 | 2.3 |
| 6 | B2 | 188 | 0.17 | — | — | — |
| 7 | A1 | 248 | 44.6 | 73.1 | 13.9 | 0.21 |
| 8 | B1 | 249 | 58.0 | 82.7 | 3.5 | 2.4 |

The results show the inferior performance of catalysts A2, A3 and B2, which are not according to the invention, and the fact that the tungsten catalysts promote both etherification and esterification, as judged by the higher amount of ether formed and the low ratio of alcohol:ester in the product.

EXAMPLES 9 AND 10

Catalysts prepared by procedures D and E of Example 1 were each employed for the hydrogenation of heptanoic acid in the liquid phase. Reactions were carried out in high pressure autoclaves of approximately 80 mls capacity. In each case 20 g n-heptanoic acid and 0.5 g catalyst were charged to the reactor, the vessel was flushed and pressurised with hydrogen gas, and then heated at 230° C. for 12 hours. The vessel was then cooled, and the products recovered and analysed by glc. The product was found to contain n-heptylheptanoate. Evidently, n-heptanol product undergoes esterification in situ with unreacted acid.

The results are reported in Table 2.

TABLE 2

| Example | Catalyst | n-heptylheptanoate concentration (wt %) |
|---|---|---|
| 9 | D | 11.9 |
| 10 | E | 13.2 |

EXAMPLES 11 AND 12

The catalyst of procedure F Example 1 was studied for the vapour phase hydrogenation of acetic acid. The experimental details were as for Examples 2-8. Results are reported in Table 3.

TABLE 3

| Example | T/°C. | Conversion (%) | Selectivity to alcohol +ester | Selectivity to alkanes |
|---|---|---|---|---|
| 9 | 182 | 25 | 58 | 41.5 |
| 10 | 204 | 43.5 | 50.5 | 49.3 |

We claim:

1. A catalyst for use in the hydrogenation of a $C_2$ to $C_{12}$ carboxylic acid to produce an alcohol and/or a carboxylic acid ester which catalyst comprises from 1 to 10% by weight of a first component which is molybdenum or tungsten from 1 to 10% by weight of a second component which is a noble metal of Group VIII of the Periodic Table of the Elements and a third component comprising the remainder of the catalyst a support which is a high surface area graphitised carbon.

2. A catalyst according to claim 1 wherein the second component is either palladium, rhodium or ruthenium.

3. A catalyst according to claim 1 wherein the second component is palladium.

4. A catalyst according to claim 1 wherein the catalyst is modified by the inclusion of one or more metals of Groups IA, IIA or IVA of the Periodic Table.

5. A catalyst according to claim 4 wherein the modifying metal is potassium.

6. A process for the production of the catalyst of claim 1 which process comprises the steps of:
(A) impregnating a high surface area graphitized carbon support with a solution of a soluble Group VIII noble metal compound thermally decomposable/reducible to the metal and subsequently removing the solvent therefrom.
(B) heating the Group VIII noble metal on the support in the presence of a gas selected from an inert gas, a reducing gas and an oxygen-containing gas, the heating being accomplished at a temperature in the range from 100° to 350° C. for an inert gas and a reducing gas and at a temperature in the range from 100° to 200° C. for an oxidising gas; and (C) impregnating the Group VIIII noble metal impregnated support with a solution of a soluble molybdenum or tungsten compound thermally decomposable/reducible to the metal and/or oxide and thereafter removing the solvent therefrom.

7. A catalyst as claimed in any of claims 1, 2, 3, 4 or 5 in which the first component is molybdenum.

8. A catalyst as claimed in any of claims 1, 2, 3, 4 or 5 in which the first component is tungsten.

9. A process as claimed in claim 6 step (C) in which the non-noble metal component is molybdenum.

10. A process as claimed in claim 6 step (C) in which the nonnoble metal component is tungsten.

* * * * *

UNITED STATES PATENT AND TRADEMARK OFFICE
CERTIFICATE OF CORRECTION

PATENT NO. : 4,826,795
DATED : May 2, 1989
INVENTOR(S) : MELANIE KITSON et al

It is certified that error appears in the above-identified patent and that said Letters Patent is hereby corrected as shown below:

Col. 1, line 10, after "of" insert --carboxylic acids to produce the corresponding alcohol and/or carboxylic acid ester--

Col. 5, line 49, should read, ".. to 50,000 $h^{-1}$, preferably from 2,000 to 30,000 $h^{-1}$.."

Signed and Sealed this

Thirty-first Day of July, 1990

Attest:

HARRY F. MANBECK, JR.

*Attesting Officer*     *Commissioner of Patents and Trademarks*